United States Patent
Towe et al.

(10) Patent No.: US 8,626,303 B2
(45) Date of Patent: Jan. 7, 2014

(54) NEUROSTIMULATOR

(75) Inventors: Bruce Towe, Mesa, AZ (US); William E. Crisp, Paradise Valley, AZ (US)

(73) Assignee: Arizona Board of Regents, a Body Corporate, Acting for and on Behalf of Arizona State University, Scottsdale, AZ (US)

(*) Notice: Subject to any disclaimer, the term of this patent is extended or adjusted under 35 U.S.C. 154(b) by 333 days.

(21) Appl. No.: 12/908,792

(22) Filed: Oct. 20, 2010

(65) Prior Publication Data

US 2011/0077722 A1 Mar. 31, 2011

Related U.S. Application Data

(63) Continuation of application No. 12/732,001, filed on Mar. 25, 2010, now Pat. No. 8,340,773, which is a continuation of application No. 10/524,955, filed as application No. PCT/US03/26002 on Aug. 19, 2003, now Pat. No. 7,702,395.

(60) Provisional application No. 60/404,697, filed on Aug. 19, 2002, provisional application No. 60/473,240, filed on May 23, 2003.

(51) Int. Cl.
 *A61N 1/36* (2006.01)
(52) U.S. Cl.
 USPC .......................................................... 607/48
(58) Field of Classification Search
 USPC .......................................................... 607/48
 See application file for complete search history.

(56) References Cited

U.S. PATENT DOCUMENTS

| | | | |
|---|---|---|---|
| 3,659,615 A | 5/1972 | Enger | 607/35 |
| 3,735,756 A | 5/1973 | Richards et al. | 601/2 |
| 5,749,909 A | 5/1998 | Schroeppel et al. | 607/33 |
| 5,957,851 A | 9/1999 | Hossack | 600/459 |
| 6,231,516 B1 | 5/2001 | Keilman et al. | 600/485 |
| 6,366,813 B1 | 4/2002 | DiLorenzo | 607/45 |
| 6,562,033 B2 | 5/2003 | Shah et al. | 606/41 |
| 6,575,894 B2 | 6/2003 | Leysieffer et al. | 607/57 |
| 6,654,638 B1 * | 11/2003 | Sweeney | 607/9 |
| 7,283,874 B2 | 10/2007 | Penner | 607/33 |
| 2005/0055073 A1 | 3/2005 | Weber | 606/2 |

FOREIGN PATENT DOCUMENTS

WO   WO-2004/105583   12/2004

OTHER PUBLICATIONS

The Master's thesis of Bioengineering student Mr. Williiarn Phillips, planned for May 2002 commencement and subsequent placement within a few months in ASU library.
An abstract submitted for review to the BMES Meeting in Houston, Texas, for presentation in Oct. of 2002.
Gavrilov, et al., Stimulation of human peripheral neural structures by focus ultrasound. Sov Phys Acoust 1974; 19(4):332-334.
Hu, et al., "Effects of low-intensity ultrasound on the central nervous system of primates," Avist Space Environ Med 1976; 47(60):640-643.

(Continued)

*Primary Examiner* — George Manuel
(74) *Attorney, Agent, or Firm* — Fulbright & Jaworski LLP

(57) ABSTRACT

Methods and devices of stimulating nerves are disclosed. In one embodiment adapted for stimulating excitable tissue, the invention includes drive circuitry (12), an acoustic transducer (14) and a pair of electrodes (28).

5 Claims, 12 Drawing Sheets

(56) References Cited

OTHER PUBLICATIONS

Takagi, et al., The actions of ultrasound on the myelinated nerve, the spinal cord, and the brain. Jpn J Physiol 1959; 10:183-193.

Mihran, et al., Temporally specific modifications of myelinated axon excitability in vitro following a single ultrasound pulse, Ultrasound in Med Biol 1990; 16(3):297-309.

Velling, et al., "Modulations of the functional state of the brain with aid of focused ultrasonic action," Neurosci Behav Physiol, 1988; 18(5):369-375.

Wells, P.N.T., Biomedical Ultrasonics, Academic Press, London, 1977 p. 15.

Office communication, issued in U.S. Appl. No. 10/524,955, dated Nov. 19, 2009.

Office communication, issued in U.S. Appl. No. 10/524,955 dated Jun. 5, 2009.

Office communication, issued in U.S. Appl. No. 10/524,955 dated Dec. 17, 2008.

Office Communication, issued in U.S. Appl. No. 10/524,955, dated Apr. 10, 2008.

Office Communication, issued in U.S. Appl. No. 10/524,955, dated Oct. 31, 2007.

* cited by examiner

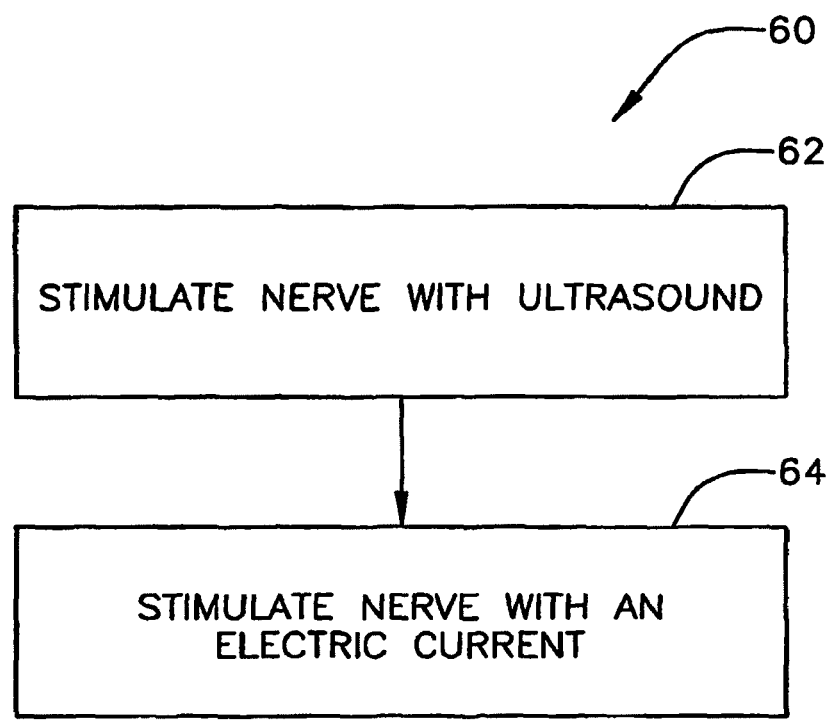

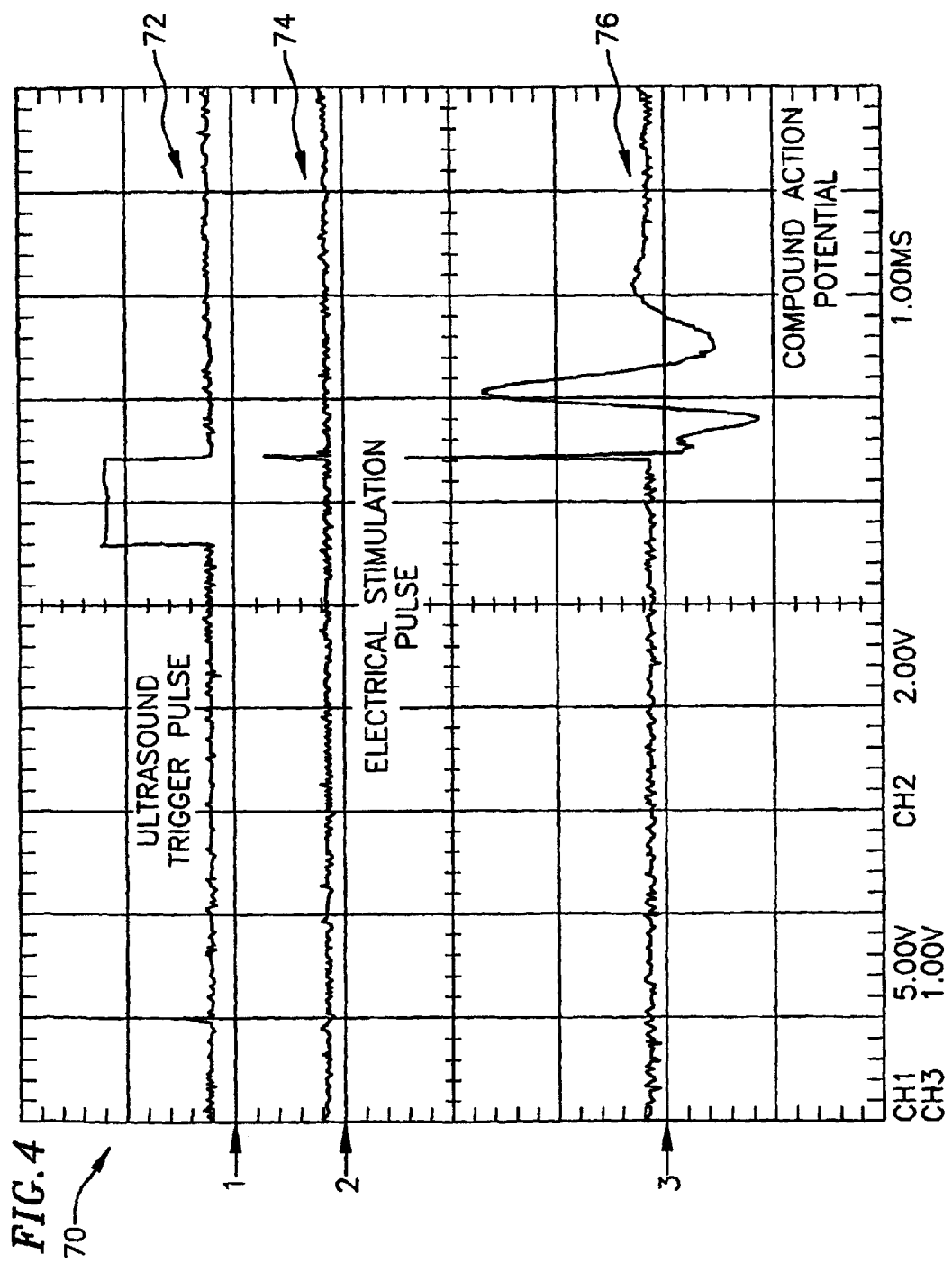

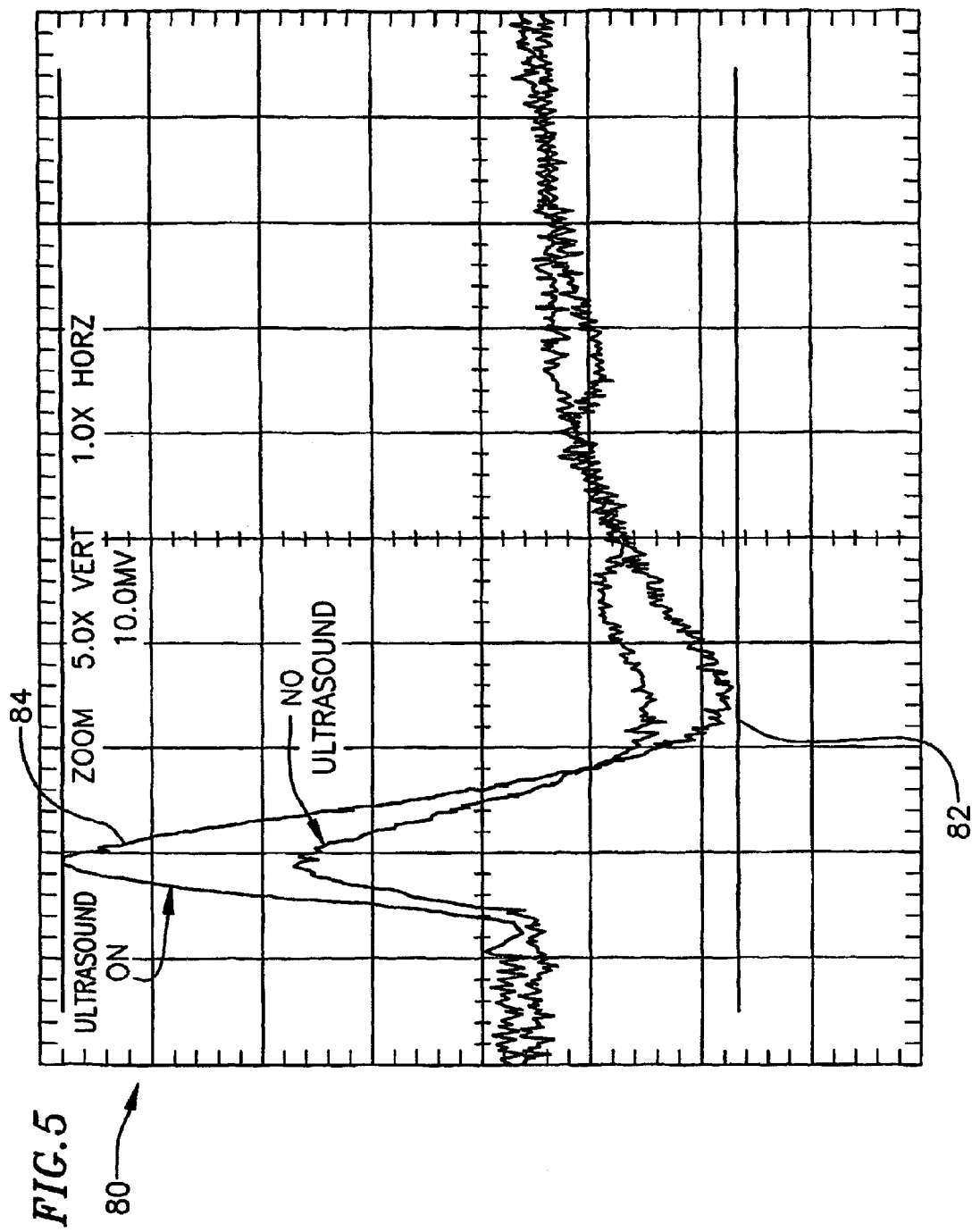

NEUROSTIMULATOR

RELATED APPLICATION INFORMATION

This application is a continuation of U.S. patent application Ser. No. 12/732,001, filed Mar. 25, 2010, which is a continuation of U.S. patent application Ser. No. 10/524,955, filed Feb. 3, 2006, now U.S. Pat. No. 7,702,395, which is a national stage entry of PCT Patent Application No. PCT/US2003/0260023, filed Aug. 19, 2003, which claims the benefit of U.S. Provisional Application Ser. No. 60/404,697, filed on Aug. 19, 2002, and U.S. Provisional Application No. 60/473,240, filed May 23, 2003, all of which are hereby incorporated by reference as if set forth fully herein.

STATEMENT OF GOVERNMENT SUPPORT

This invention was made with government support under grant numbers R21 RR1330602 and R41 NS42978-01 awarded by the National Institutes of Health. The government has certain rights in the invention.

BACKGROUND OF THE INVENTION

The present invention relates generally to devices and methods for performing neural stimulation and more specifically to devices and methods that employ ultrasound to achieve neural stimulation.

Nerves in higher biological organisms are bundles of long, excitable cells that can extend to meter-order lengths. Cells are referred to as excitable when they are capable of responding to various electric, chemical, optical, and mechanical stimuli by changing their cell transmembrane potential (TMP). A cell's TMP is a measure of the potential difference across the cell's membrane. A TMP can be created due to different concentrations of ions on either side of the membrane. Cells typically maintain lower concentrations of ions inside the cell than the concentration of ions outside the cell to prevent the cell from swelling due to osmosis. Therefore, cells typically have a TMP or are depolarized.

A localized stimulus to an excitable cell, known as an action potential, can affect the cell's TMP. The reduction in TMP causes the cell's membrane to allow sodium ions to rush into the cell, which further reduces the cell's TMP. The reduction of the TMP is known as depolarization. A cell without TMP will swell due to osmosis, therefore, shortly after the sodium inrush the cell expels potassium through the cell membrane. Reducing the potassium concentration inside the cell decreases charge within the cell and increases the TMP. The process of restoring a cell's TMP is known as repolarization.

During the time when the cell is depolarized, it cannot be restimulated by another action potential. This interval is known as the cell's absolute refractory period. The cell's relative refractory period is the interval from partial to complete repolarization. During this time, the cell can be restimulated, but a higher stimulus is required to produce an action potential event, and the response of the excitable cell is lower in magnitude.

Nerve cells are a particular type of excitable cell that are typically characterized by a cell body from which extend dendrites and an axon. The long axon is coated in myelin sheaths and axon terminals extend from the end of the axon. When the nerve cell is stimulated, a depolarization wave travels down the axon to the axon terminals. The axon terminals respond to the depolarization wave by releasing specialized chemicals known as neurotransmitters. The neurotransmitters bind to receptors in the dendrites of adjacent nerve cells and depending on the type of receptor that is activated, will either excite or inhibit the generation of an action potential in the adjacent cell. In this way, signals are passed from one nerve cell to another and enable impulses to be carried along nerve fibers.

Neurostimulation is a term used to describe the artificial excitation or inhibiting of nerve cells. Neurostimulation is thought to be desirable as either a tool for simulating nerve function or for inhibiting the flow of information to the brain (e.g. blocking pain impulses). The ability to selectively stimulate specific nerve fibrils in a complex nerve bundle containing thousands, is a long sought capability in biomedical research. One method has been to try and stimulate the nerves using an electrode. However, placing an electrode in contact with the desired nerve fibril can be invasive. Alternatively, a nerve cuff electrode can be used. Nerve cuff electrodes typically involve placing multiple electrodes around the nerve to create an electric field designed to stimulate a specific nerve fiber.

SUMMARY OF THE INVENTION

Methods and apparatus are described that enable the stimulation of neurons using a combination of ultrasound and electric currents. In one aspect of the invention, high frequency ultrasound and electric currents are used to stimulate neurons. In a further aspect of the invention, ultrasound is used to excite devices that include piezoelectric materials, which generate electric currents for stimulating neurons.

In one embodiment, the invention includes drive circuitry, an acoustic transducer and a pair of electrodes. In addition, the drive circuitry can be configured to drive the acoustic transducer to generate a pressure wave, the acoustic transducer can be positioned to direct the pressure wave at excitable tissue and the drive circuitry can be configured to generate stimulating current between the pair of electrodes.

In a further embodiment, the pair of electrodes are implemented using a piezoelectric chip, the drive circuitry is configured to drive the acoustic transducer to generate a pressure wave and the acoustic transducer is positioned to direct the pressure wave towards the piezoelectric chip.

In another embodiment, the piezoelectric chip includes a piezoelectric element having at least two opposite surfaces, rectifying circuitry, a biocompatible coating surrounding the piezoelectric element and the diode and an electrode located adjacent each of the opposite surfaces, where each electrode is partially contained by the biocompatible coating. In addition, the piezoelectric element can include zirconate titanate (PZT). In a still further embodiment, the piezoelectric element can include polyvinylidene fluoride (PVDF).

In yet another embodiment, the invention can include additional piezoelectric chips. In addition, each of the piezoelectric chips can have a different resonant frequency and the drive circuitry can be configured to drive the acoustic transducer at the resonant frequency of one of the piezoelectric chips.

In a still further embodiment again, the drive circuitry includes a pulse generator, a function generator connected to the pulse generator and amplifier circuitry connected to the function generator. In addition, the amplifier circuitry can include a drive amplifier and a RF amplifier.

In one embodiment, the method of the invention includes applying stimulating ultrasound to tissue and applying a stimulating electric current to the tissue.

In another embodiment, the method of the invention includes directing pressure waves at a piezoelectric chip located proximate excitable tissue.

BRIEF DESCRIPTION OF THE DRAWINGS

FIG. 3 is a flow chart illustrating a method in accordance with the present invention that can be used to either stimulate or inhibit the creation of a compound action potential in a nerve fiber;

FIG. 4 is a graph showing a compound action potential generated in response to neurostimulation in accordance with the present invention;

FIG. 5 is a graph comparing the compound action potentials generated using electrical stimulation alone and using ultrasound and electrical stimulation in accordance with an embodiment of the present invention;

DETAILED DESCRIPTION OF THE INVENTION

Turning now to the drawings, novel approaches to achieving neurostimulation are presented involving devices and methods that utilize electric currents and/or ultrasound. In one embodiment, high frequency ultrasound is used in combination with electric currents to achieve neurostimulation. In another embodiment, piezoelectric chips implanted proximate a nerve fiber are used to convert ultrasound energy into sufficient electric current to achieve neurostimulation.

Figure 1:
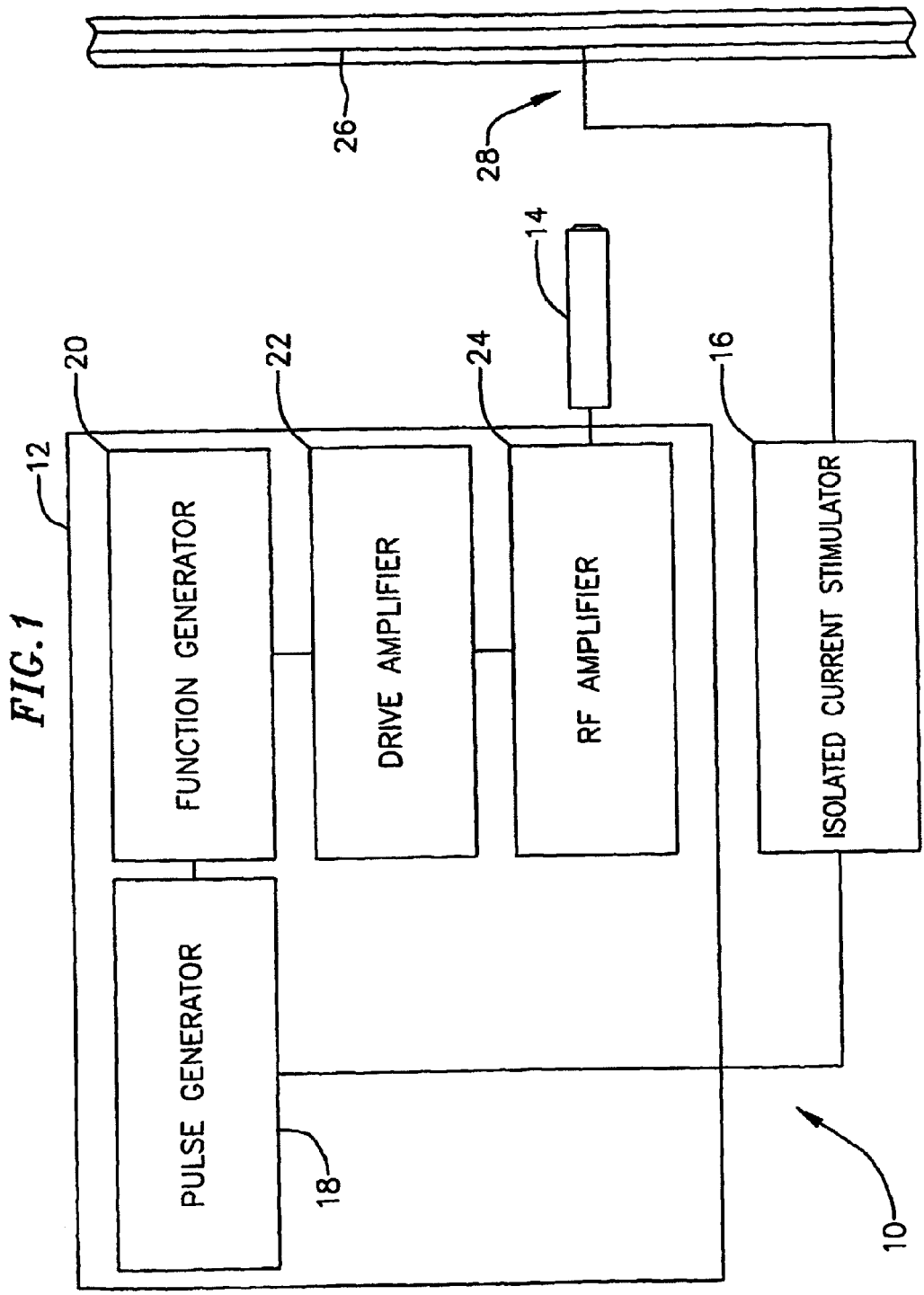
FIG. 1 is a block view of an embodiment of a neurostimulator in accordance with the present invention.

Turning now to FIG. 1, a neurostimulator in accordance with the present invention is illustrated. The neurostimulator 10 includes drive circuitry 12 that is connected to an ultrasound transducer 14 and a current stimulator 16. The drive circuitry includes a pulse generator 18 that is connected to a function generator 20 and the current stimulator 16. The function generator 20 is connected to a drive amplifier 22. The drive amplifier is connected to an RF amplifier 24, which provides an output to the ultrasound transducer 14. The ultrasound transducer is focused at a nerve fiber 26 and the current stimulator is connected to electrodes 28 that are positioned proximate the nerve fiber.

In embodiments, where the nerve fiber is contained within a subject's body, the electrode may be located external to the subject or internal to the subject. Where the electrodes are external to the subject, the electrodes are typically positioned around the ultrasound transducer. Where the electrodes are internal to the subject, one electrode is typically placed as close to the nerve as possible and another electrode is placed on the other side of the stimulating pressure wave generated by the ultrasound transducer. Although other configurations that create sufficient electric currents in the region the ultrasound is stimulating can also be used.

The drive circuitry can generate electric signals that drive the ultrasound transducer and the current stimulator. The ultrasound transducer can use these signals to generate pressure waves for stimulating nerve fibers. The electrode can also stimulate nerve fibers by generating electric currents. In one embodiment, the pulse generator provides a pulse to the function generator and the current stimulator. The pulse can trigger the function generator to produce a high frequency sinusoidal signal, which is then provided to the drive amplifier. The drive amplifier and the RF amplifier combine to increase the power of the high frequency sinusoidal signal to the level required for the ultrasound transducer to generate pressure waves of sufficient power. A pulse can also prompt the current stimulator to generate a signal, which generates a desired electric current between electrodes. In one embodiment, the combination of the pressure waves generated by the ultrasound transducer and the electric currents generated by the electrodes cause a compound action potential in the nerve fiber. In another embodiment, the combination of the pressure waves generated by the ultrasound transducer and the electric currents generated by the electrodes can inhibit the generation of a compound action potential in the nerve fiber.

Figure 2:
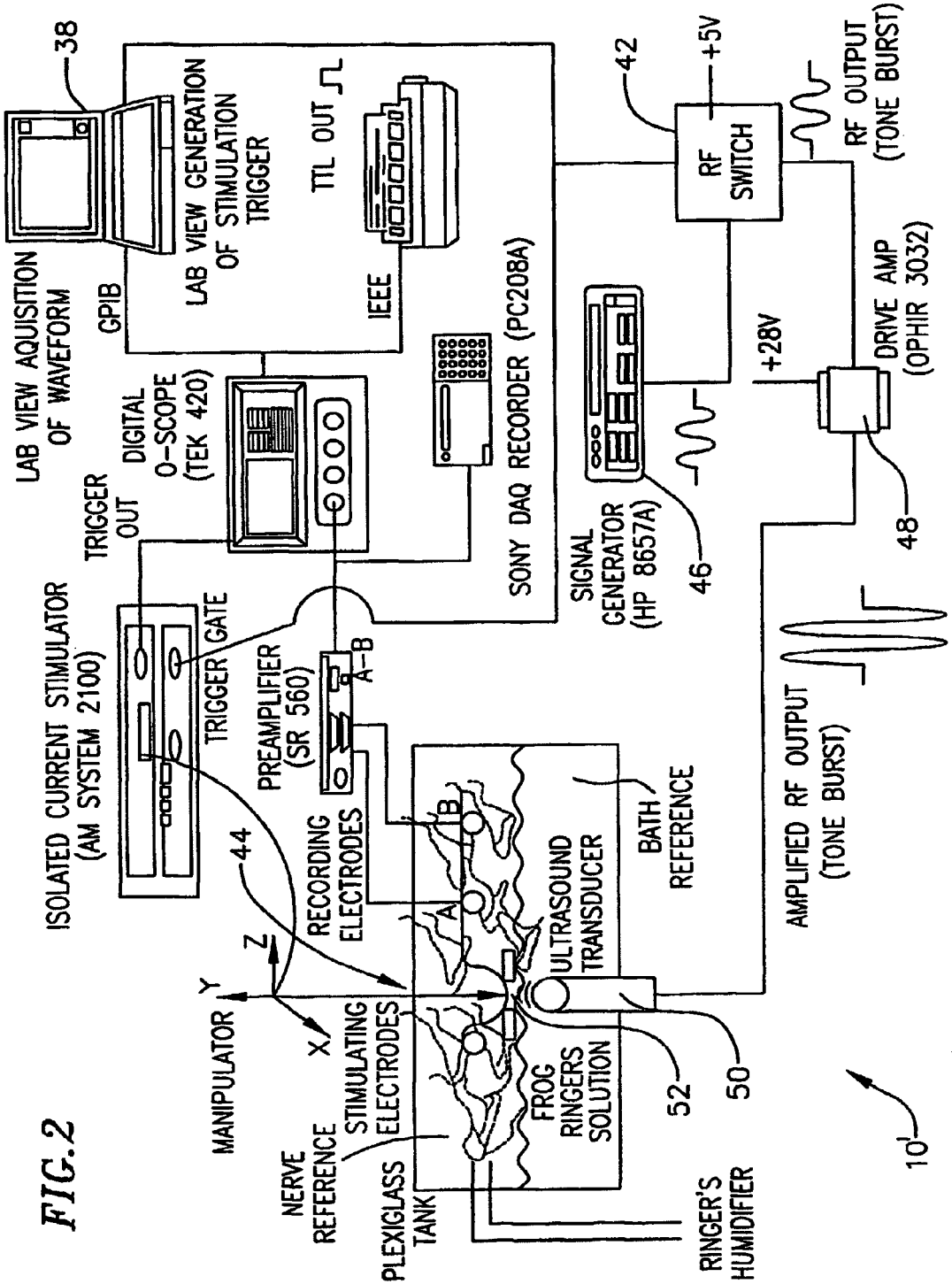
FIG. 2 is a schematic diagram that schematically illustrates an embodiment of a neurostimulator in accordance with the present invention.

A neurostimulator in accordance with the present invention is illustrated in FIG. 2. The neurostimulator 10' includes a computer 38. The computer is connected to an isolated current stimulator 40 and an RF switch 42. The isolated current stimulator is connected to electrodes 44. The RF switch is connected to a signal generator 46 and a drive amplifier 48. The output of the drive amplifier is provided to an ultrasound transducer 50. The ultrasound transducer is focused on a frog nerve 52 that is contained in a chamber 54 filled with Ringer's solution 56.

In one embodiment, the computer uses a software package such as LABVIEW, created by National Instruments Corporation of Austin, Tex. to generate stimulation trigger pulses. The computer can generate the trigger pulses using an output card such as a model DAQ1200 card manufactured by National Instruments Corporation. The trigger signal can be used to synchronize current delivery from the isolated current stimulator, which can be implemented using a model 2100 manufactured by A-M Systems, Inc. of Sequim, Wash. The output of the isolated current stimulator is provided to the electrodes, which can be 500 μm silver wire stimulating electrodes spaced by 3 mm. Although in other embodiments, other electrodes suitable for use in biomedical applications involving the generation of electric currents can be used. The output of the signal generator can be provided to the RF switch, which is gated to pass the RF signal in response to trigger pulses from the computer.

In one embodiment, the signal generator can be implemented using a Model 8657A manufactured by the Hewlett Packard Company of Palo Alto, Calif. and the RF switch can be implemented using a Model 50S-348 manufactured by JFW Industries, Inc. of Indianapolis, Ind. The output of the RF switch is provided to the drive amplifier, which can drive the ultrasound transducer.

In one embodiment, the drive amplifier is implemented using a Model 3032 manufactured by Ophir RF of Los Angeles, Calif. and the ultrasound transducer is produced by a miniature transducer manufactured by Valpey Fisher Corporation of Hopkinton, Md. that has a 1 mm diameter, is 125 μm thick, is lightly damped and has a lithium niobate radiating element.

In addition to the embodiments described above, one of ordinary skill in the art would appreciate that other components that perform similar functions and different configurations of components can be used that are capable of providing appropriate drive signals to electrodes and an ultrasound transducer. In addition, one of ordinary skill in the art can appreciate that the dimensions and materials used in the construction of the ultrasound transducer are a function of the wavelength of the pressure waves that are sought to be generated by the transducer. A discussion of the variation in compound action potential response associated with the wavelength of the pressure waves generated by the pressure transducer is provided below.

A process in accordance with the present invention for stimulating a nerve fiber is illustrated in FIG. 3. The process 60 includes stimulating the nerve fiber with ultrasound 62 and stimulating the nerve fiber with an electric current 64. In one embodiment, the ultrasound stimulation is applied for a time period and the electrical stimulation is applied at the end of the time period.

A graph is illustrated in FIG. 4 that shows the timing of the application of ultrasound stimulation, electrical stimulation and the subsequent generation of a compound action potential. The graph 70 includes 3 plots. The uppermost plot 72 is of the ultrasound trigger pulse. For the duration of the ultrasound trigger pulse, ultrasound stimulates the nerve fiber. The middle plot is of the electrical stimulation pulse 74. The electrical stimulation pulse is used to generate an electric current for stimulating the nerve fiber. The electrical stimulation pulse is triggered at approximately the end of the ultrasound trigger pulse. The lower plot 76 shows the nerve response. The application of the electrical stimulation pulse creates a compound action potential.

In the illustrated embodiment, an ultrasound pre-pulse is used to stimulate the nerve fiber. Observations have shown that ultrasound can be nominally effective in causing changes in nerve excitability for several milliseconds after cessation of an ultrasound pre-pulse. The time that ultrasound causes an effect on nerve fibers varies with the ultrasound frequency, pulse duration, duty cycle and other factors. Typically, the nerve will remain stimulated for a period of between 3 milliseconds and several seconds. In other embodiments, simultaneous application of ultrasound and electrical stimulation is effective in generating a compound action potential. Alternately, other embodiments of the invention can use ultrasound pulses to provide an initial stimulation and then following a delay, trigger an action potential using electrical stimulation.

In the embodiment illustrated in FIG. 4, an ultrasound pulse with a frequency of 20 MHz and an electrical stimulation pulse of less than 1 mA were used to stimulate the nerve fiber. When ultrasound is used to stimulate a nerve fiber, the amplitude of the electrical stimulation required to generate a compound action potential can be reduced. Alternatively, the magnitude of the compound action potential can be increased.

A graph is illustrated in FIG. 5 that shows the effect of using ultrasound to stimulate a nerve in addition to electrical stimulation. The graph 80 includes two plots. The first plot 82 shows the compound action potential generated when electrical stimulation alone is used to stimulate an in-vitro frog sciatic nerve. The second plot 84 shows the compound action potential generated when ultrasound and electrical stimulation are used to stimulate the same nerve. The magnitude of the compound action potential increases with the addition of ultrasound stimulation. In the illustrated embodiment, the applied ultrasound was a pulse of a duration of 10 ms and a peak power of approximately 100 W/cm$^2$. In other embodiments, fully saturated nerve responses have been obtained using ultrasound and an electrical stimulus that would recruit as little as 10% of the cells in the nerve fiber without the use of ultrasound.

Embodiments of the present invention, as described above, are capable of using a variety of frequencies of ultrasound to stimulate a nerve fiber. Some embodiments are effective at generating compound action potentials when ultrasound with a frequency of between 15 MHz and 100 MHz is used. Frequencies outside this range can also be effective in generating action potentials, but can require higher power levels to achieve the same effectiveness. The following table shows the effect of the frequency of the ultrasound used to stimulate a nerve on the magnitude of the compound action potential achieved using a fixed electrical stimulating pulse.

TABLE 1

Effect of Frequency on Ultrasound Evoked Bioelectric Stimulation Events

| Ultrasound Frequency | Number of Trials | Relative Bioelectric Effect of Ultrasound Stimulation Weighted for Power Compared to 17.5 MHz |
|---|---|---|
| 17.5 MHz | 10 | 1.0 |
| 56.5 MHz | 10 | 3.4 ± 1.2 |
| 93 MHz | 2 | 3.0 ± 0.7 |

The above table illustrates that the magnitude of a generated compound action potential varies with frequency. A theory has been proposed concerning the effectiveness of various ultrasound frequencies at generating compound action potentials. Devices and methods of the present invention do not in any way rely upon theories presented here in order to be effective in generating compound action potentials. However, applicants propose that applying pressure forces to ion channels in cell membranes decreases the potential required to open the ion channels and stimulates the creation of an action potential.

Figure 6A:
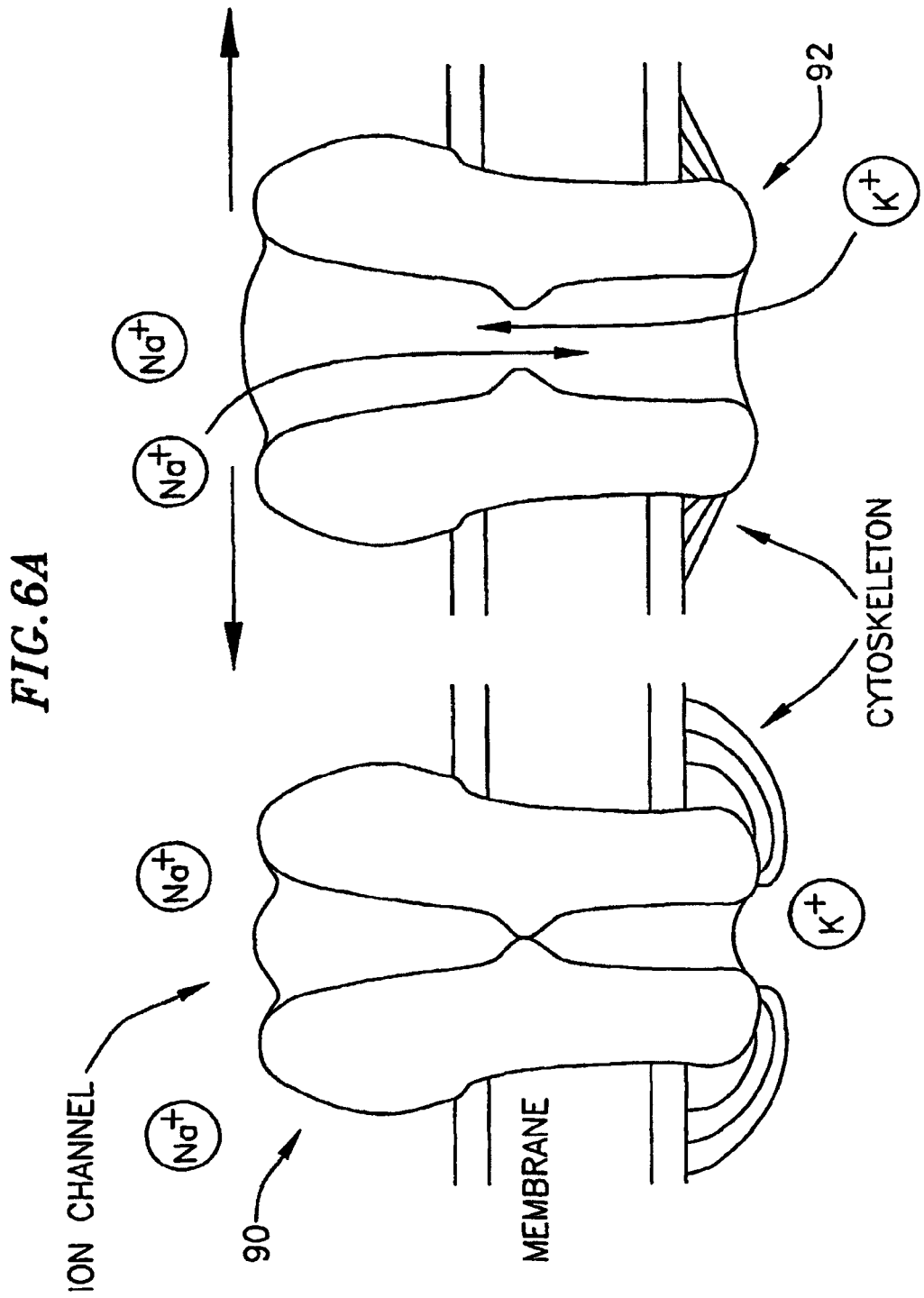
FIGS. 6A and 6B are schematic diagrams illustrating the effect of the wavelength of pressure waves generated in accordance with an embodiment of the present invention on ion channels in nerve cell membranes.

The effect of pressure on an ion channel is illustrated in FIG. 6A. An ion-channel 90 is illustrated that is not exposed to ultrasound. The ion channel is closed and creates an effective barrier between the interior of the cell and extracellular fluids. A second ion channel 92 is illustrated. The second ion channel is stretched due to a pressure wave traveling through the cell. The pressure wave stretches the cell membrane, which opens the ion channel and allows ions to pass in and out of the cell.

Figure 6B:
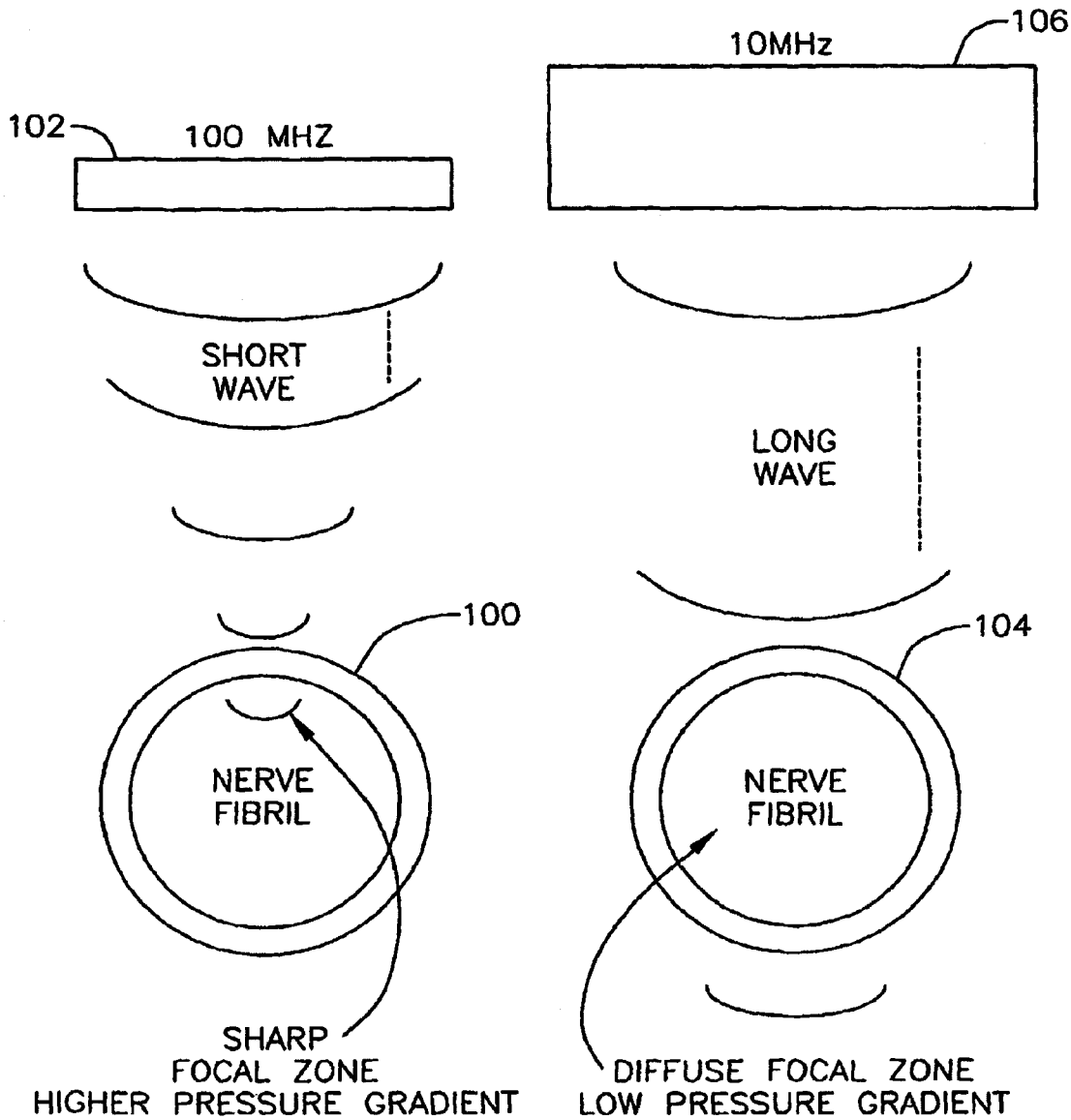

The impact of wavelength (i.e. frequency) on the ability of a pressure wave to open ion channels in cell membranes is illustrated in FIG. 6B. Two nerve fibrils are illustrated. The first nerve fibril 100 is excited using a 100 MHz ultrasound transducer 102 in accordance with the present invention. The short wavelength of the pressure wave (not to scale) generated by the 100 MHz ultrasound transducer is comparable to the dimensions of the fibril and the fibril's membrane. The second nerve fibril 104 is excited using a 10 MHz ultrasound transducer. The longer wavelength (not to scale) of the pressure wave generated by the 10 MHz ultrasound transducer results in a pressure wave that is several orders of magnitude larger than the size of the nerve fibril. Stretching of cell membranes results from pressure differentials at different locations in the pressure wave. When a pressure wave has a wavelength of a similar order to a nerve fibril, the forces experienced by the cell membrane of the fibril will be significant because the entire pressure differential between the peak and the trough of the pressure wave is experienced by the cell.

When constructing embodiments of the present invention in accordance with the techniques described above, the frequency of the ultrasound chosen is important. Ultrasound waves in the VHF region (30-100 MHz) are more strongly absorbed by tissue and have less penetration compared to the diagnostic frequencies below about 10 MHz. Ultrasound intensity along a beam path declines exponentially. Experiments have determined that the effective penetration depths in tissue to the 10% intensity point will be on the order of a centimeter at 30 MHz and millimeters at 100 MHz. Therefore, systems in accordance with the present invention that require ultrasound to penetrate through significant amounts of bone or flesh to stimulate a neuron can be subject to a tradeoff between the desire to increase frequency to produce the strongest stimulatory effect and trying to reduce frequency in order to penetrate to the required depth.

The penetration depth of a particular frequency of ultrasound can be increased by using lenses to focus the ultrasound generated by an ultrasound transducer. A focused wave can spread a large amount of energy over a large area at the surface and enable a significant amount of that energy to converge on the focal point, despite absorption.

In one embodiment, lenses for focusing ultrasound can be constructed using molded epoxies that are applied to the ultrasound transducer. Focal spot sizes of just a few wavelengths are possible and can give energy concentration ratios of several hundred. This offers the potential to obtain a much greater penetration depth when the target area is very small. Additionally, ultrasound can be projected into tight beams and reach effective intensity at some distance from the transducer face.

The characteristics of the ultrasound pulses are important in achieving neurostimulation. In one embodiment, ultrasound pulses having a pulse length of between 300 µs and 10 ms are used and the pulses are repeated with a repetition rate of between 1 pulse per second and 10 pulses per second. When the length of the pulse is decreased, the effectiveness of the ultrasound in stimulating a nerve fiber is decreased. Increasing the duration of the pulse beyond 50 ms can have the effect of causing nerve damage due to the amount of energy transferred by the pulses.

As observed previously, embodiments of the present invention may be used to inhibit compound action potentials as an alternative to stimulating compound action potentials. Experimental results have yielded the conclusion that the repetition rates and duration of ultrasound pulses determine whether a stimulatory or inhibitory effect is achieved. In addition, results have also shown that the pulse characteristics that will achieve stimulatory effects and inhibitory effects are repeatable for each preparation. However, results have also shown that the characteristics vary from preparation to preparation. Therefore, one of ordinary skill in the art would appreciate that varying the characteristics of ultrasound pulses may be required for different subjects in order to achieve the desired stimulatory or inhibitory effect.

In several of the embodiments described above penetration depth can be a problem, because the ultrasound transducers are located external to the subject. In other embodiments, one or more ultrasound transducers can be located on a nerve cuff electrode. Locating ultrasound transducers on a nerve cuff electrode enables focused ultrasound that can target specific fibers. In one embodiment, a nerve cuff is used that includes an array of ultrasound transducers of sub-millimeter size around the circumference of the nerve cuff and each ultrasound transducer can be electrically addressed.

Many neurostimulation systems require the generation of electric fields using electrodes that are connected via wires to driving circuitry. When a nerve fiber located within a subject's body is sought to be stimulated, electrodes are typically either implanted into the subject or attached to the surface of the subject's body. Implanting of electrodes is invasive and typically requires that leads connecting the electrodes to external driving circuitry emerge from the subject's body. When electrodes are located on the surface of the subject, the electrical field required to stimulate the nerve fiber may exceed the pain threshold of the skin.

Figure 7:
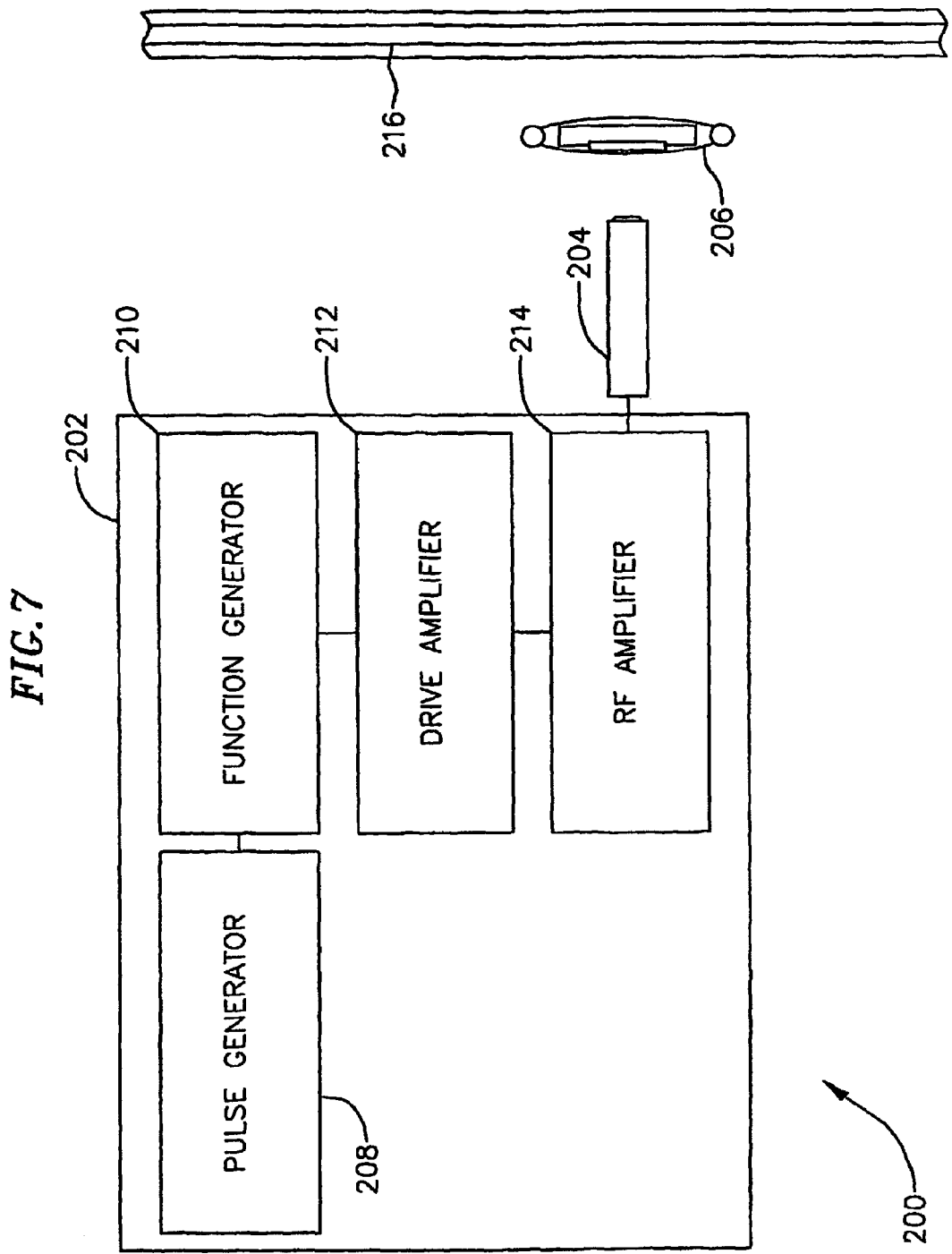
FIG. 7 is a schematic view of an embodiment of a neurostimulator in accordance with the present invention that uses an embedded piezoelectric chip to generate electric fields.

A neurostimulator that uses an implanted piezoelectric chip as an electrode is illustrated in FIG. 7. The neurostimulator 200 includes driving circuitry 202 connected to an ultrasound transducer 204 and at least one piezoelectric chip 206. The driving circuitry includes a pulse generator 208 that is connected to a function generator 210. The function generator is connected to a drive amplifier 212, which in turn is connected to an RF amplifier 214. The output of the RF amplifier is provided to the ultrasound transducer. The piezoelectric chip is located proximate a nerve fiber 216.

The drive circuitry 202 generates a drive signal that is provided to the ultrasound transducer. The drive signal enables the ultrasound transducer to generate a desired pressure wave in a manner similar to that described above in relation to FIG. 1. The ultrasound transducer is positioned to create a pressure wave that is incident on the piezoelectric chip. The excitation of the piezoelectric materials in the piezoelectric chip generates an electric current that can then be used to stimulate an action potential or inhibit the creation of an action potential in a nerve fiber.

The ability to ultrasonically cause nerve action events using implanted piezoelectric chips can depend on the physics of piezoelectric materials used in the piezoelectric chips, electric field propagation in nonhomogeneous volume conductors, as well as acoustics. Ultrasound pulses averaging an intensity of 10-100 mW/cm$^2$ in the range of 2.5-7.5 MHz can evoke milliamperes from small chips of piezoelectric materials immersed in a medium having a physiologic conductivity.

Electrical waves at MegaHertz ultrasound frequencies are relatively long in wavelength compared to body dimensions. This means that the piezoelectric chip can be considered as a near field electrical source coupled by a complex impedance to electrodes.

Figure 8:
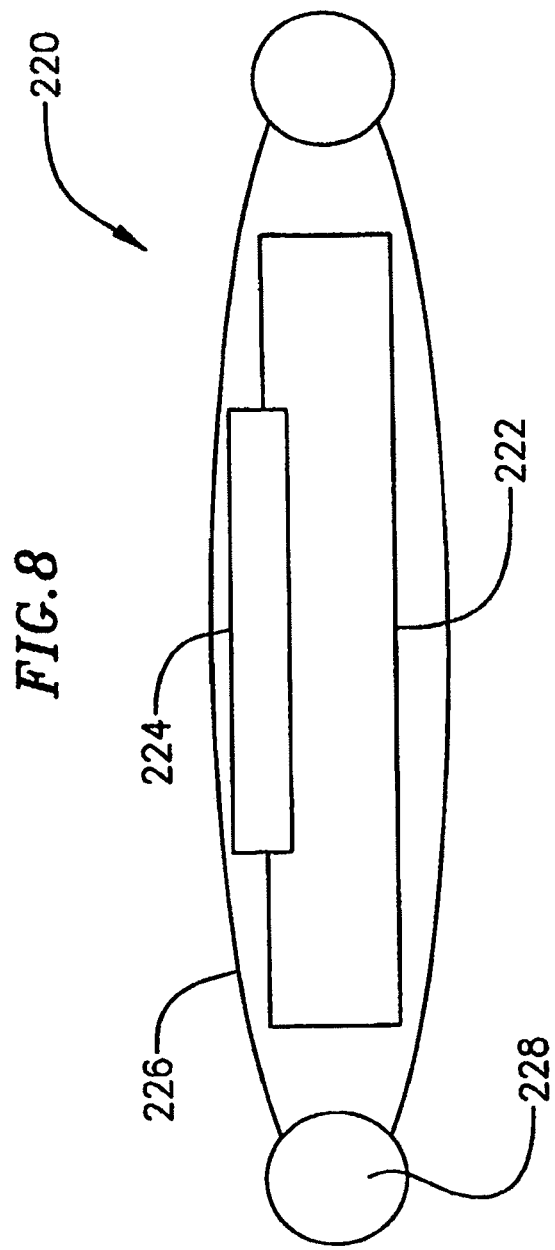
FIG. 8 is a schematic view of an embodiment of a piezoelectric chip in accordance with the present invention.

An embodiment of a piezoelectric chip in accordance with the present invention is illustrated in FIG. 8. The piezoelectric chip 220 includes a thin piezoelectric element 222 to which a diode 224 is attached. The piezoelectric element and the diode are encased in a biocompatible coating 226. A pair of electrical contacts 228 are partially embedded within the biocompatible coating at opposite ends of the piezoelectric chip.

The piezoelectric element can be constructed from a piezoelectric material, which is a material that generates a current when pressure is applied to the surface of the material. This class of materials includes polymers like polyvinylidene fluoride (PVDF), ceramics like lead zirconate titanate (PZT) and crystals like quartz. When piezoelectric materials are placed in a volume-conducting medium so that the surfaces of the material contact the solution, the generated potentials can be significant and sufficient to stimulate compound action potentials from nerve fibers.

When choosing a piezoelectric material to construct the piezoelectric element, the amount of energy in the pressure wave incident on the piezoelectric element that is converted into an electric field is important to the efficiency of the system. The acoustic impedence of the piezoelectric material relative to tissue determines how much ultrasound energy is actually absorbed and turned into charge. The rest of the energy is reflected at the interface between the sound transport medium and piezoelectric material. This relationship can be determined from $$R=[(Z1-Z2)/(Z1+Z2)]^2$$

Where R is the fraction of incident sound power reflected from the surface of PZT while the remainder enters, and Z1 and Z2 are the acoustic impedance's of the materials.

In tissue, calculations estimate that embodiments of the present invention that use PZT will reflect approximately 90% of incident energy. Embodiments that use PVDF are estimated to reflect approximately 11% of incident energy, because the PVDF polymer has an acoustic impedance much closer to that of tissue.

In practice, factors such as electrical power transfer (as defined by the electrical port impedance of the materials) and how materials match to tissue electrical impedance at a desired ultrasound frequency can influence design decisions. A piezoelectric material's dielectric constant and its self-capacitance are significant factors in determining port impedance. For low impedance conductive media such as tissue, the lower port impedance of PZT can make it preferable to a material with a higher port impedance such a PVDF, despite the greater theoretical efficiency of PVDF in converting energy from a pressure wave into an electric field.

In one embodiment of a piezoelectric chip adapted for use inside human tissue, the piezoelectric element is constructed using a piece of PZT that has a thickness of 100 µm, a width of 1 mm and a length of 3 mm. A piezoelectric element with these dimensions can be inserted into a subject using a 16 gauge needle. In other embodiments, piezeo elements can be constructed using pieces of PZT of various sizes. The larger the volume of the piezoelectric element, the greater the current that can be generated using the piezoelectric element. In one embodiment, the piezoelectric element is constructed using the material PZT-5A manufactured by Boston Piezo-Optics, Inc of Bellingham, Mass. Other piezoelectric materials can also be used, which would be dimensioned according to the voltage and current requirements of the particular application. Examples of other piezoelectric materials that could be used include any piezoceramic, Lithium Niobate, quartz, Lead Metaniobate, Lead Titanate, Tourmaline or any other material that will generate a potential when excited by a pressure wave.

In other embodiments, the piezoelectric element can be constructed using multiple pieces of piezoelectric material connected in electrical series to increase the potential generated by the piezoelectric element by a factor proportionate to the number of pieces of piezoelectric material and to decrease the current generated by the same factor. These embodiments can be useful in circumstances where the electrode resistance is high and additional voltage is required to generate a stimulating current.

It is well known that nerves respond to electrical impulses over certain ranges of duration and amplitude. The frequency of the electrical currents generated by piezoelectric chips as a result of stimulation using ultrasound are typically of a frequency that is too high to stimulate a compound action potential. In the illustrated embodiment, a diode is used to rectify the current generated by the piezoelectric element. The combination of half-wave rectification and the capacitance of the two electrodes in the piezo chip (i.e. the electrode equivalent capacitance) smooth the generated current to provide a pulse with a duration proportionate to the duration of the ultrasound pulse used to stimulate the piezoelectric element. Therefore, appropriate choice of the ultrasound pulse duration can ensure that the generated current is capable of stimulating a compound action potential. In embodiments, where the electrode equivalent capacitance is insufficient to provide the required smoothing, a capacitor can be connected between the electrodes to increase the electrode equivalent capacitance. In one embodiment, a 1n34A industry standard germanium diode is used to provide half wave rectification. In other embodiments, Shotcky diodes, silicon diodes or an integrated diode bridge could be used to rectify the current generated by the piezoelectric element. In other embodiments, other circuits that convert the current generated by the piezoelectric element to a current capable of stimulating a compound action potential can be used.

In one embodiment the biocompatible coating serves to insulate the electrical interconnects within the piezoelectric chip and is constructed using a polyimide such as PYRALIN 2721 manufactured by E.I. DuPont Nemours and Company of Wilmington, Del. In other embodiments, other coatings such as biocompatible epoxies or biocompatible polymers that are preferably transparent to sound can be used in the construction of a biocompatible coating. When a photoresist material such as PYRALIN is used in the construction of the piezoelectric chip, the biocompatible coating can be applied to the entire chip and then the electrodes can be partially exposed using photoresist techniques.

In other embodiments, the biocompatible coating can be loaded using additives such as Tungsten that increase the acoustic impedance of the biocompatible coating to enable more efficient acoustic power transfer from the tissue medium to the piezoelectric element. In addition, the amount of energy in a pressure wave that is converted into electrical energy by a piezoelectric chip in accordance with the present invention can be increased by acoustic impedance matching the thickness of the biocompatible coating with the frequency of the pressure waves. Typically, impedance matching can be achieved by using a biocompatible coating having a thickness that is approximately equal to one quarter of the wavelength of the pressure waves being used to stimulate the piezoelectric chip.

The electrodes can serve the function of transferring electrical current from the piezoelectric element to stimulate an ionic current flow in a conductive fluid and in one embodiment are constructed using a chromium based stainless steel alloy such ELGILOY manufactured by Elgiloy Specialty Metals in Elgin, Ill. In other embodiments, other biocompatible electrode materials such as platinum, silver, iridium oxide, tantalum can be used in the construction of the electrodes.

Figure 9:
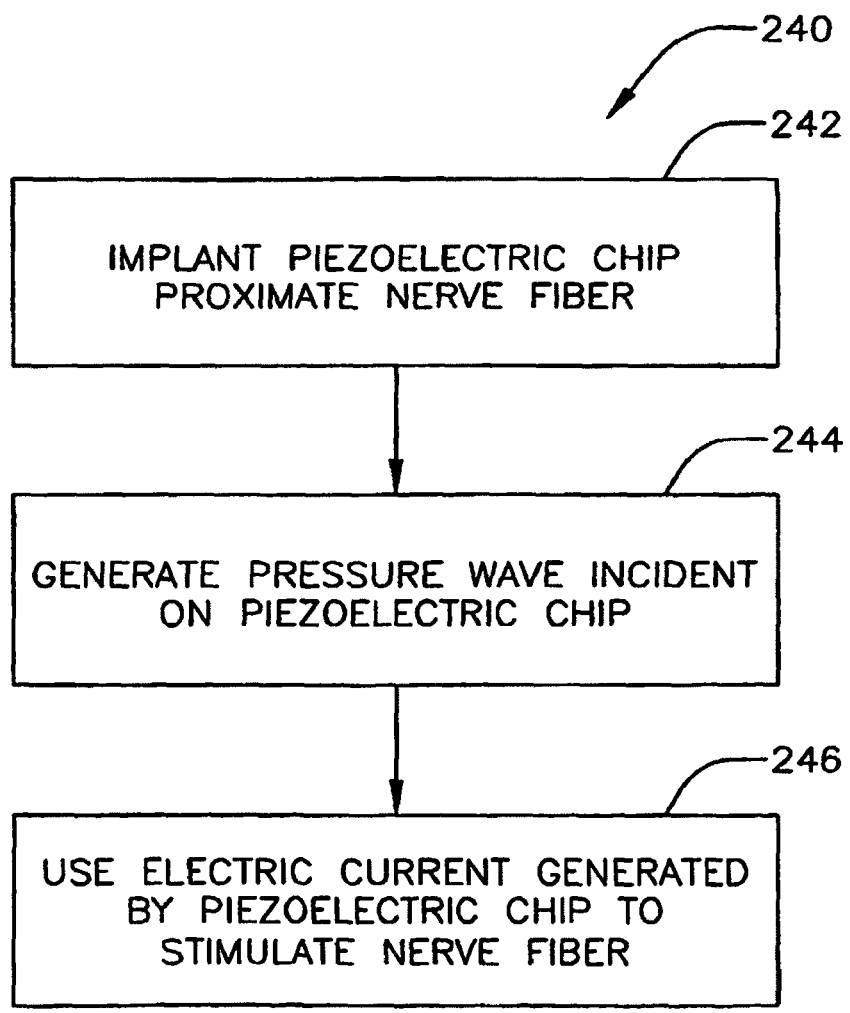
FIG. 9 is a flow chart illustrating a method in accordance with the present invention for performing neurostimulation using a piezoelectric chip that is capable of generating an electric field when illuminated by ultrasound.

A flowchart for stimulating a nerve fiber in accordance with the present invention is illustrated in FIG. 9. The process 240 includes implanting a piezoelectric chip proximate the nerve fiber, generating a pressure wave incident on the piezoelectric chip 244 and using an electric current generated by the piezoelectric chip to stimulate the nerve fiber 246.

In one embodiment, the piezoelectric chip is designed to be small enough to be implanted close to the nerve fiber using a standard gauge syringe. The pressure wave incident on the piezoelectric chip can have similar frequencies to a pressure wave generated by a medical diagnostic system, as described above. The pulse duration and amplitude of the pressure wave is typically chosen such that a piezoelectric chip can generate a current capable of stimulating a compound action potential in the manner described above. In several embodiments, a modified medical imaging ultrasound transducer can be used that is capable of locating the piezoelectric chips using reflected ultrasound and then switching modes to stimulate the located chips using appropriate ultrasound pulses.

In other embodiments other frequencies and powers can be used depending on the size and the type of piezoelectric chip, the distance of the piezoelectric chip from the nerve fiber and the electric current required to generate a desired compound action potential. The electric current generated by the piezoelectric chip in response to excitation by pressure waves is dependent on the factors described above. In other embodiments, a combination of an electric current generated by the piezoelectric chip and pressure waves generated by an ultrasound transducer can be used to stimulate the nerve fiber (see above).

Figure 10:
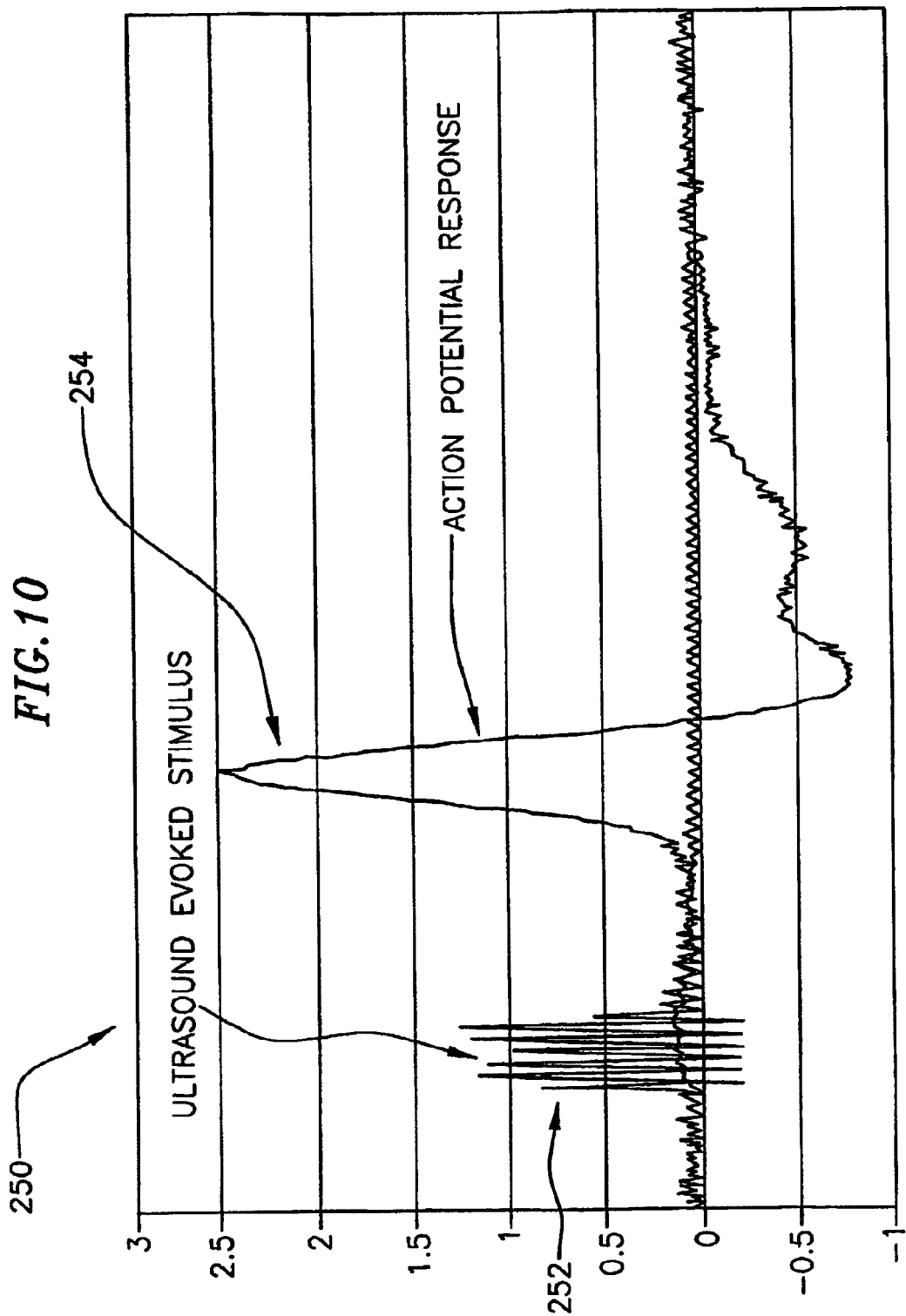
FIG. 10 is a graph showing the generation of a compound action potential in response to neurostimulation via an electric field generated by a piezoelectric chip in accordance with the present invention.

A graph showing the generation of a compound action potential in response to an electric field generated by a piezoelectric chip, on which a pressure wave is incident is illustrated in FIG. 10. The graph 250 includes two plots. The first plot 252 shows the ultrasound stimulated electric field generated by the piezoelectric chip. The second plot 254 shows the compound action potential generated in response to the stimulating electric field.

The resonance of a piezoelectric material is a function of the ratio of the ultrasound wavelength to the material thickness. A thickness of piezoelectric material equal to a half-wavelength of the incident ultrasound tends to increase the power transferred to the piezoelectric material and increase the voltage output by the piezoelectric chip. This is particularly true of high-Q piezoceramics like PZT, which mechanically ring at their natural resonant frequency. Therefore, the electric currents generated by piezoelectric chips will tend to be relatively larger at their resonant frequencies. This means that an array of piezoelements, each having a different natural frequency, can be implanted into the body and thus be actuated individually by selection of applied ultrasound frequency.

Figure 11:
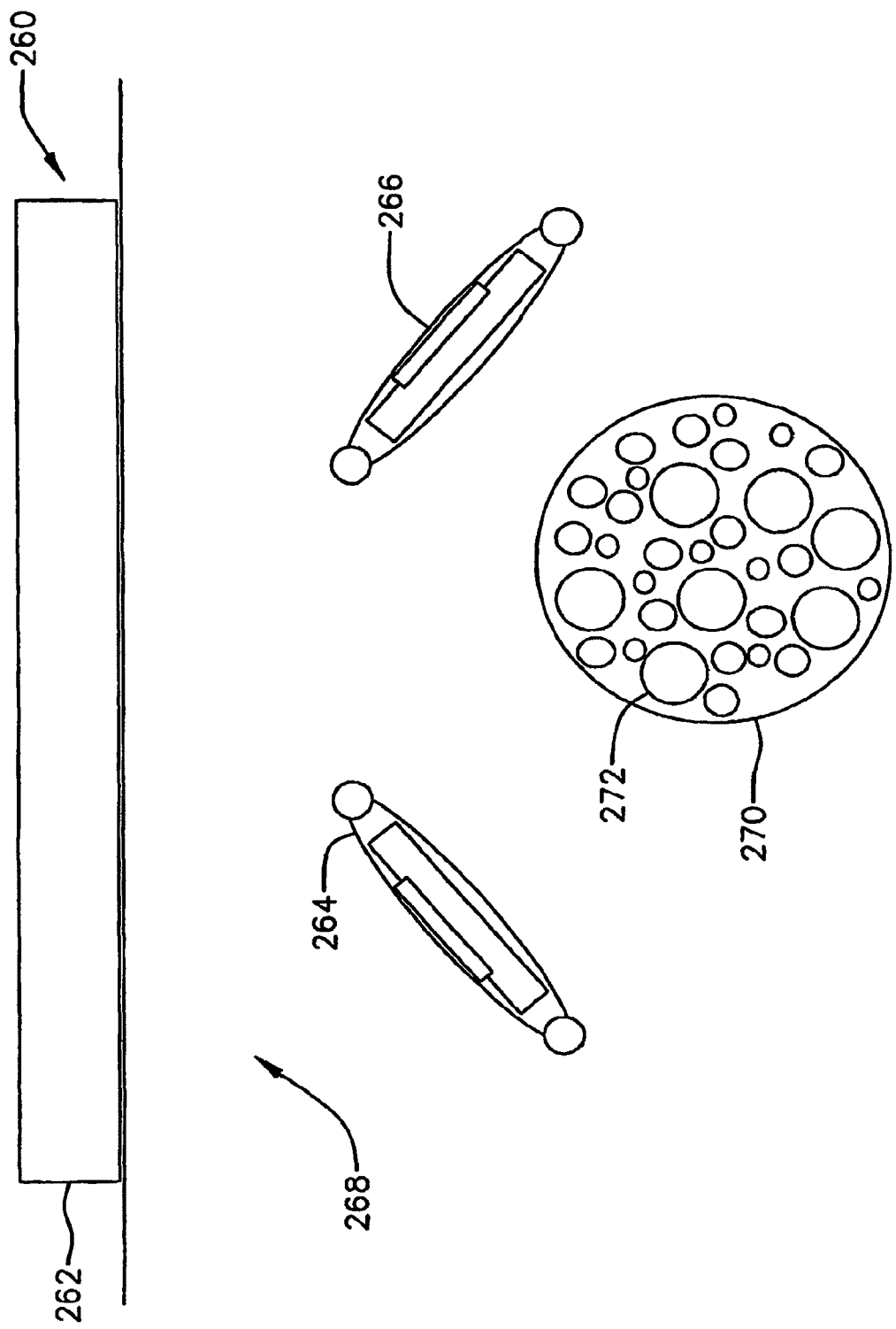
FIG. 11 is a schematic view illustrating the excitation of a number of piezoelectric chips with ultrasound energy in accordance with an embodiment of a the present invention.

The use of a multiple piezoelectric chips to selectively stimulate nerve fibers in accordance with the present invention is illustrated in FIG. 11. The neurostimulator includes an ultrasound source that is capable of generating multiple frequencies of ultrasound and a first piezoelectric chip 264 and a second piezoelectric chip 266. The first and second piezoelectric chips are implanted in tissue proximate a nerve bundle 270 including a number of nerve fibers 272. Each piezoelectric chip can be constructed to have a different resonant frequency. Generating pressure waves with a frequency corresponding to the resonant frequency of one of the piezoelectric chips results in that piezoelectric chip generating a significantly stronger electric field. Therefore, different frequencies of ultrasound can be used to selectively stimulate different nerve fibers using different piezoelectric chips. Alternatively, multiple chips with the same resonant frequency can be selectively stimulated by focused pressure waves or simultaneously stimulated using a single ultrasound transducer.

In one embodiment, neurostimulators in accordance with the present invention can be used to stimulate the pudental nerve. Urinal incontinence can be combated by stimulation of the pudental nerve. Patients are often reluctant to undergo treatment using conventional neurostimulators, because the intensity of the required electric currents can cause pain and/or discomfort. Therefore, neurostimulation in accordance with the present invention involving the use of ultrasound stimulation can reduce the intensity of electric currents required and/or the use of an implanted piezoelectric chip as an electrode can reduce the electric field required at the surface of the subject's body and enable treatment without discomfort.

The same advantages are also available when embodiments of the present invention are used as a substitute for conventional transcutaneous electronic nerve stimulators (TENS). Pulsed electrical currents in the milliampere range can block pain impulses traveling up the spine. This works by stimulating large fast nerve fibers, which block pain sensations from slower sensory nerves. Conventional TENS devices can cause a tolerable but uncomfortable shocking sensation at the electrodes, because the electrical currents required to be effective are themselves not far from the threshold that produces pain from skin receptors. As described above, embodiments of the present invention can be used to provide the benefits of TENS while reducing the likelihood of pain or discomfort.

Although the foregoing embodiments are disclosed as typical, it will be understood that additional variations, substitutions and modifications can be made to the system, as disclosed, without departing from the scope of the invention. For example, animal subjects may be used in addition to human subjects, when applying neurostimulation in accordance with the present invention. In addition, the discussion presented above has focused on neurostimulation. Other embodiments of the present invention may be used to stimulate various excitable tissue types such as muscle tissue.

What is claimed is:

1. A receiver-stimulator device comprising:
    a plurality of acoustic transducers, each comprising an implanted piezoelectric chip, that receive acoustic energy from an acoustic source and generate acoustic energy to generate an electric current;
    a demodulator connected to each transducer receive the electrical signals and rectify the signals to a biologically stimulating electrical output; and at least two tissue contacting stimulation electrodes coupled to each demodulator which receive the stimulating electrical output and deliver said output to tissue; and
    wherein the contributions of the plurality of acoustic transducers are placed in series such the electric output of each transducer is additive.

2. The device of claim 1, wherein the plurality of transducers are positioned such that a resulting transducer array is substantially symmetrical and annular.

3. The device of claim 1, wherein the electrodes are nerve cuff electrodes disposed around a nerve.

4. The device of claim 3, wherein the nerve cuff electrodes stimulate a specific nerve fiber.

5. The device of claim 3, wherein the transducers are ultrasound transducers of sub-millimeter size disposed around the circumference of the nerve cuff and each ultrasound transducer is electrically addressed.

* * * * *